United States Patent
Asefa et al.

(10) Patent No.: US 8,802,045 B2
(45) Date of Patent: Aug. 12, 2014

(54) MESOPOROUS AND NANOPOROUS MATERIALS, AND METHODS OF SYNTHESIZING THE SAME

(75) Inventors: Tewodros Asefa, Manlius, NY (US); Richard E. Mishler, II, Baldwinsville, NY (US); Eric A. Schiff, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 954 days.

(21) Appl. No.: 12/797,722

(22) Filed: Jun. 10, 2010

(65) Prior Publication Data

US 2010/0313937 A1    Dec. 16, 2010

Related U.S. Application Data

(60) Provisional application No. 61/185,870, filed on Jun. 10, 2009.

(51) Int. Cl.
| | |
|---|---|
| *C01B 31/36* | (2006.01) |
| *C01B 33/12* | (2006.01) |
| *C07C 45/00* | (2006.01) |
| *C07C 67/08* | (2006.01) |

(52) U.S. Cl.
CPC ............... *C01B 33/12* (2013.01); *C07C 45/00* (2013.01); *C07C 67/08* (2013.01)
USPC .......................................................... 423/335

(58) Field of Classification Search
CPC ............... C01B 33/12–33/193; C07G 77/395; C07C 45/00; C07C 67/08
USPC .................. 423/335–340; 556/405; 568/388; 560/231
See application file for complete search history.

(56) References Cited

PUBLICATIONS

Aliev et al., "Porous silica and polysilsesquioxane with covalently linked phosphonates and phosphonic acids," J. Mater. Chem., 2000, 10, 2758-2764.*
Corriu et al., "Ordered SBA-15 mesoporous silica containing phosphonic acid groups prepared by a direct synthesis approach," Chem. Commun., 2001, 763-764.*
Jin et al., "Porous Silica Nanospheres Functionalized with Phosphonic Acid as Intermediate-Temperature Proton Conductors," J. Phys. Chem. C 2009, 113, 3157-3163.*
Stucky et al., "Triblock copolymer syntheses of Mesoporous Silica with Periodic 50 to 300 Angstrom Pores," Science vol. 279, Jan. 23, 1998, 548-552.*
Mishler II, Richard E., et al.,Solvent-washable polymer templated synthesis of mesoporous materials and solid-acid nanocatalysts in one-pot, The Royal Society of Chemistry 2009 Chem. Commun., 2009, pp. 6201-6203.

* cited by examiner

*Primary Examiner* — Anthony J Zimmer
(74) *Attorney, Agent, or Firm* — George R. McGuire; Frederick J. M. Price; Bond Schoeneck & King, PLLC

(57) ABSTRACT

A method for synthesizing a phosphonic acid functionalized mesoporous metal oxide material (e.g., silica, titania, alumina, preferably silica material) is provided. Further, a method of using the phosphonic acid functionalized mesoporous silica material as a solid acid catalyst in a pinicole-pinacolone rearrangement reaction, and a method of using a phosphonic acid functionalized mesoporous silica material as a solid acid catalyst in a transesterification reaction is provided. A method for preparing a mesoporous titania film for use in a dye sensitized solar cell is also provided.

7 Claims, 17 Drawing Sheets

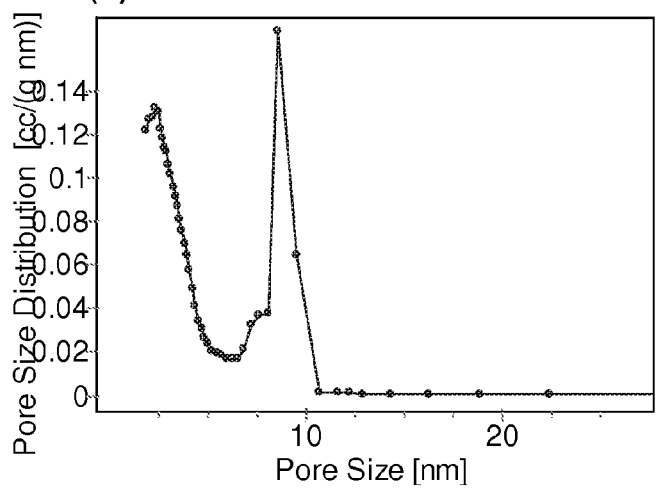
FIG. 9(A) SBA15$^P$ - sw
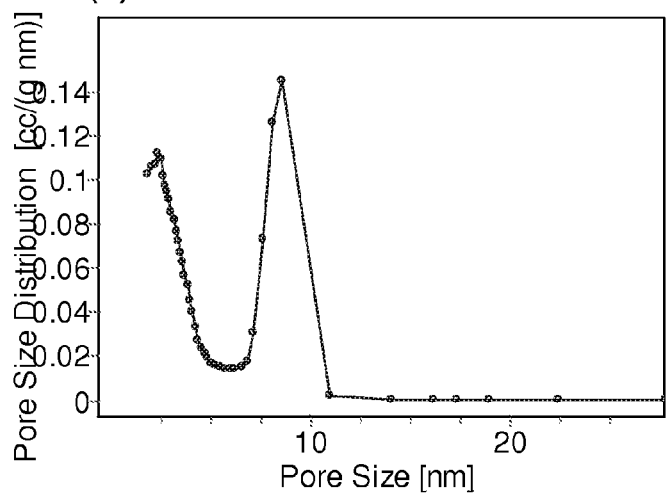
FIG. 9(B) SBA15$^P$ – cal
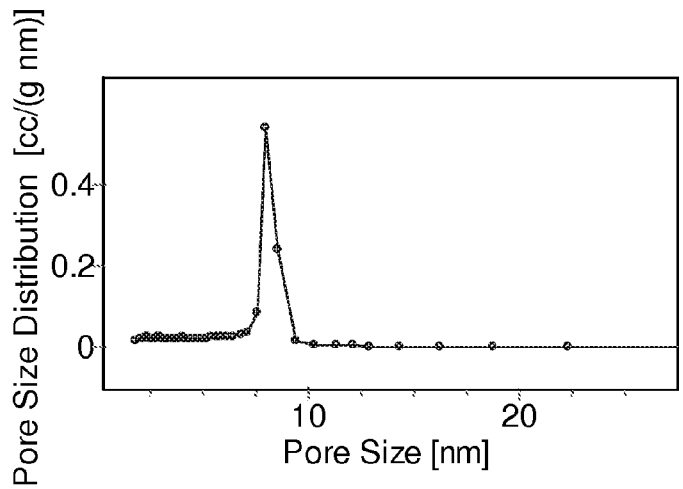
FIG. 9(C) SBA15- sw

FIG. 11(A) SBA15-sw
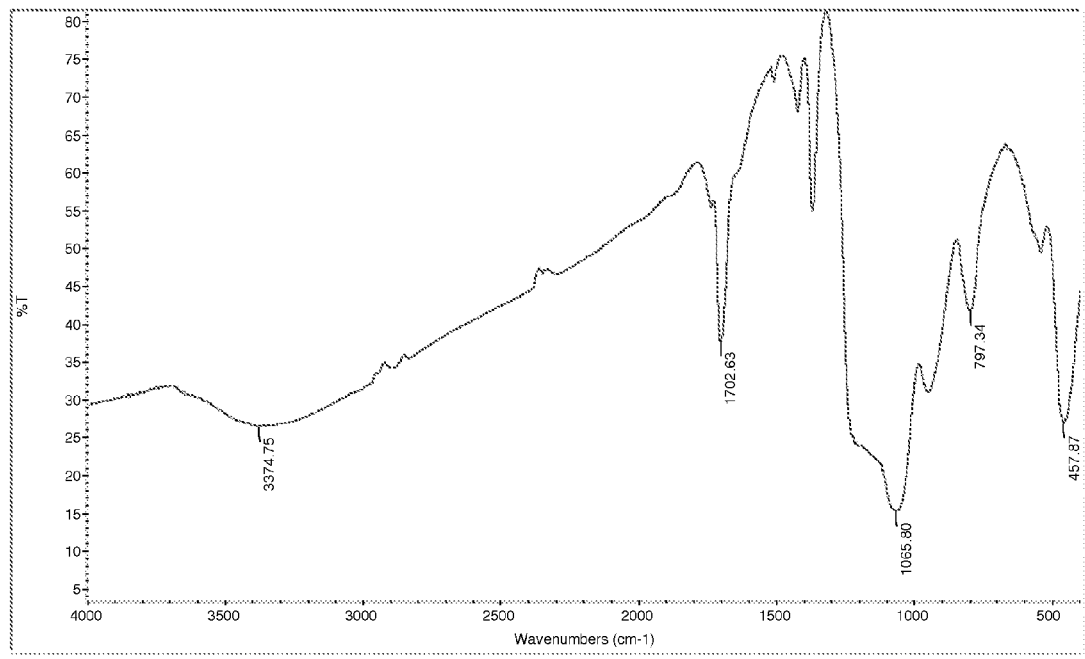
FIG. 11(B) SBA15$^P$-sw
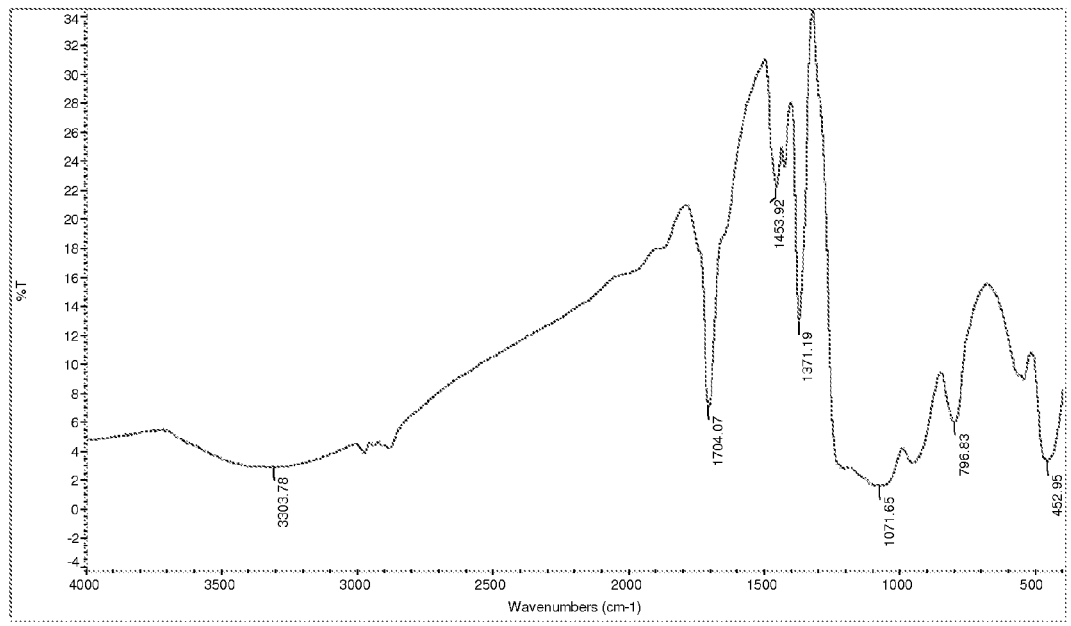

FIG. 11(C)  SBA15-Cal
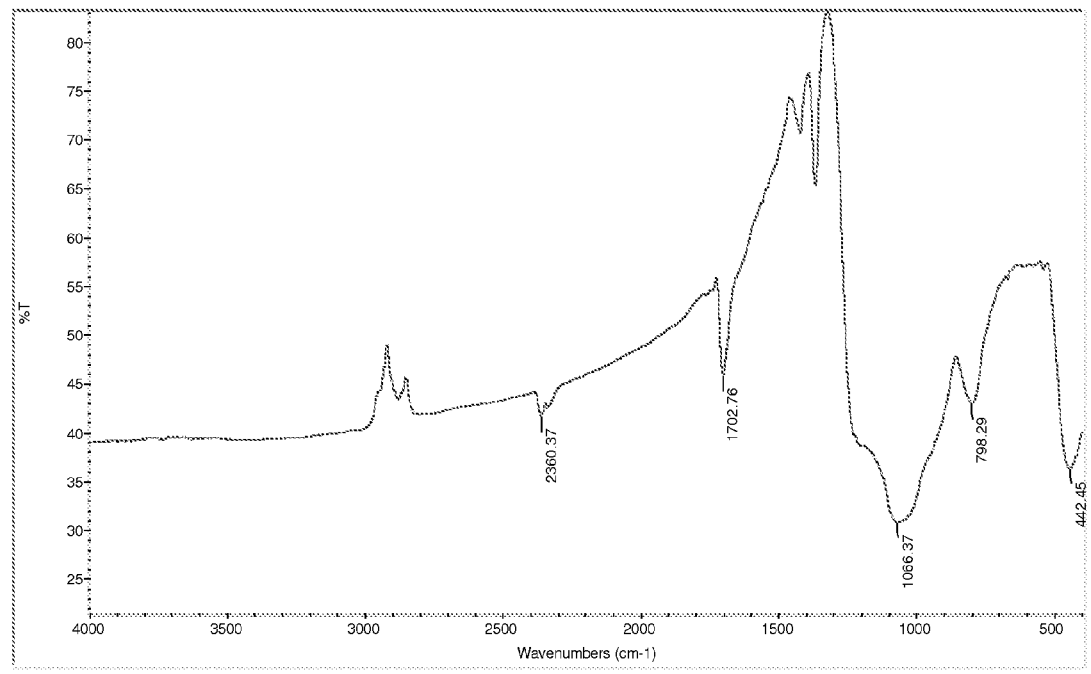
FIG. 11(D)  SBA15$^P$cal
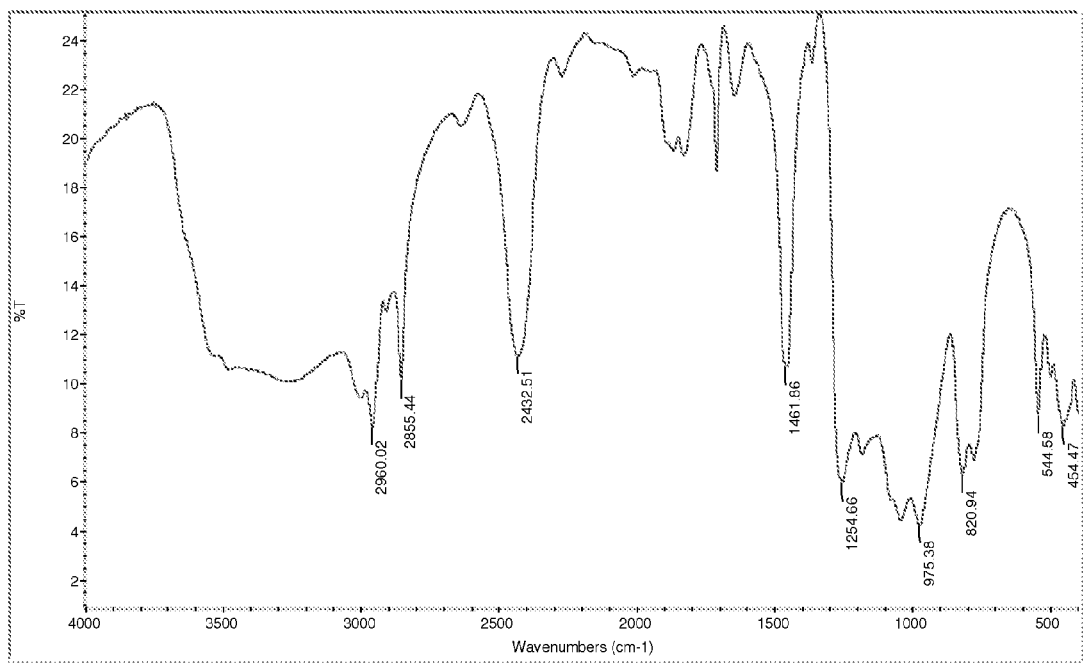

(A)

(C)

MESOPOROUS AND NANOPOROUS MATERIALS, AND METHODS OF SYNTHESIZING THE SAME

RELATED APPLICATION

The present application claims priority to U.S. provisional patent application No. 61/185,870, filed on Jun. 10, 2009; all of the foregoing patent-related document(s) are hereby incorporated by reference herein in their respective entirety(ies).

BACKGROUND OF THE INVENTION

1. Field of the Invention

The present invention relates to mesoporous and nanoporous materials and, more particularly, to highly ordered mesoporous materials and the synthesis of the same by using a phosphonated polymer template.

2. Description of the Related Art

In the early 1990's, a family of mesoporous MCM-type (Mobil Corporation) materials was discovered that has a broad range of uses including sensors, catalysis, drug delivery, and solar cells. Depending upon the inorganic material, surfactant templates, and synthetic conditions employed, mesoporous materials with widely varying composition, structure and pore sizes can be synthesized. The first report in 1998 on the synthesis of SBA-type mesoporous materials with very large pore diameter by using triblock copolymer templates was also a significant advance in the field of mesoporous materials chemistry. SBA-type materials allow the immobilization via "host-guest" inclusion processes of larger molecules that are unable to diffuse in the MCM-type mesoporous materials.

The synthesis of well-ordered mesoporous structures requires an extraction step to remove the polymer template molecules. The most common method is calcination, which involves heating the material to a temperature sufficient to oxidize the organic or polymer template. Calcination is widely used in SBA-type materials. Although extraction of polymer templates by calcination can completely remove the templates, the fairly high temperature often causes condensation of surface hydroxyl (—OH) groups on the mesoporous framework and reduction of the number of hydroxyl groups that are often utilized for further organic functionalization of the material. Calcination also modifies the framework, typically by shrinkage, and of course the template, which might otherwise be recycled, is lost.

The second method is solvent-extraction, which is often able to remove ionic templates, but has been less successful in removing non-ionic templates such as tri-block copolymers that are hydrogen-bonded to and occluded in the framework. Other methods include soxhlet extraction, stirring in supercritical fluids and stirring under reflux conditions.

A solar cell is a two-terminal electronic device that delivers electric power to an external load when the cell is illuminated by sunlight, which is the direct source of the electrical power. An important class of solar cells was patented in 1992 by Gratzel and Liska ("Photo-electrochemical cell and process of making same", U.S. Pat. No. 5,084,365 issued 1992). This cell is based on the use of a porous or mesoporous metal oxide electrode. The device is sensitized to light by attaching dyes and other chromophore molecules to the internal surfaces of the electrode. The complete device is an photo-electrochemical cell incorporating both an electrolyte or polymer that fills the porous material and also a counterelectrode that is in electrical contact with the electrolyte. Because of the common use of dyes as the chromophore molecules, this cell is usually referred to as a "dye-sensitized solar cell" (DSSC). Of particular importance have been mesoporous titanium dioxide electrodes created by sintering of dense titanium dioxide and related microparticles and nanoparticles at temperatures of about 450° C. Intrinsically mesoporous metal oxide materials such as the SBA-type materials noted earlier have also been used because of the greater ordering and control of the pore structure compared to sintered materials. These materials have been prepared starting with solutions of templating polymers that self-assemble into a desired structure, and that serve as the scaffold for the metal oxide. This second class of materials have used a process step of high-temperature calcination to burn off the templating polymer molecules, leaving behind the mesoporous metal oxide material.

Description of the Related Art Section Disclaimer: To the extent that specific publications are discussed above in this Description of the Related Art Section (as well as throughout the application), these discussions should not be taken as an admission that the discussed publications are prior art for patent law purposes. For example, some or all of the discussed publications may not be sufficiently early in time, may not reflect subject matter developed early enough in time and/or may not be sufficiently enabling so as to amount to prior art for patent law purposes. To the extent that specific publications are discussed above in this Description of the Related Art Section (as well as throughout the application), they are all hereby incorporated by reference into this document in their respective entirety(ies).

SUMMARY OF THE INVENTION

The present invention recognizes that there are potential problems and/or disadvantages in the above-discussed synthetic methods of preparing well-ordered mesoporous structures. One potential problem is that the previous synthetic methods involve the use of non-phosphonated triblock copolymer templates and their self-assembly, followed by calcination (or high temperature decomposition) to remove the templates. One class of these copolymers is known as poloxamer (non-proprietary) and by tradenames such as Pluronic®. A related problem is that the prior methods do not produce phosphonic acid functionalized mesoporous materials from the polymer template in one-pot. With respect to the conventional DSSCs referenced above, a problem relates to the solar conversion efficiency and the cost of fabrication of these cells. Sintered materials that are presently used are typically processed at temperatures of about 450° C., which increase manufacturing cost. A related problem is that sintered mesoporous materials are not well ordered, have reduced surface densities of hydroxyl groups, and are affected by pore shrinkage during sintering. These problems affect the conversion efficiency of DSSCs. Various embodiments of the present invention may be advantageous in that they may solve or reduce one or more of the potential problems and/or disadvantages discussed above in this paragraph.

It is therefore a principal object and advantage of the present invention to provide a method to synthesize highly ordered, high surface area containing mesoporous and nanoporous materials by removing templates under low temperature conditions, without calcination and decomposition of block copolymer templates.

It is another object and advantage of the present invention to provide a method to synthesize mesoporous and nanoporous materials where their structures remained intact.

It is a further object and advantage of the present invention to provide a method to synthesize solid-acid nanomaterials and nanoporous catalysts in one-step (one-pot).

It is also an object and advantage of the present invention to provide a synthetic method to produce metal oxides such as mesoporous titania, which can have appropriate structures for making better dye sensitized solar cells.

It is another object and advantage of the present invention to provide a synthetic method to produce phosphonic acid functionalized mesoporous titania with improved adsorption capacity for dyes (or sensitizers) for solar cells and consequently dye-sensitized solar cells with improved efficiency.

In accordance with the foregoing objects and advantages, an embodiment of the present invention provides mesoporous and nanoporous materials and, more particularly, highly ordered mesoporous materials and the synthesis of the same by using a phosphonated template. As described herein, the mesostructured materials were synthesized using phosphonated tri-block copolymers, and characterized.

In accordance with an embodiment of the present invention, a method is provided for phosphonating nonionic tri-block copolymer molecules, and self-assembling these phosphonated template molecules under aqueous solutions to produce highly ordered mesostructured silica, titania, alumina and other related materials. The phosphonated triblock co-polymer templates may be removed from the meso structured materials using dilute acidic solutions to produce highly ordered mesoporous silica, titania, alumina and other related materials. The phosphonated triblock co-polymer templates may be removed from the mesostructured materials leaving phosphonated groups, and these groups may be acidified into phosphonic acids to form solid-acid nanostructured materials and solid-acid nanocatalysts. The resulting solid acid nanomaterial may be used as a catalyst for acid catalyzed reactions such as pinicole-pinacolone rearrangement.

It is a further object and advantage of the present invention to provide a route for solving the above issues related to conventional DSSCs by providing a solar cell, in particular a DSSC which uses a solvent-washed, templated-mesoporous metal oxide, preferably a solvent-washed, templated-mesoporous $TiO_2$ as an electrode which has the advantages of lower energy-cost of production, reduced disorder in the mesoporous $TiO_2$, higher surface densities of hydroxyls for attachment of chromophores, re-usable template molecules, and possible concomitant improved solar conversion efficiencies.

BRIEF DESCRIPTION OF THE DRAWINGS

The present invention will be more fully understood and appreciated by reading the following Detailed Description in conjunction with the accompanying drawings, in which:

FIG. 9 is a graphical illustration showing pore size distribution of template extracted samples (A) SBA15$^P$-sw, (B) SBA15$^P$-cal, and (C) SBA15 according to an embodiment of the present invention.

FIG. 11 is a graphical illustration showing FT-IR spectra of SBA15 sample after (a) solvent washing (SBA15-sw), (b) calcination (SBA15-cal); and SBA15$^P$ sample after, (c) solvent washing (SBA15$^P$-sw) and (d) calcination (SBA15$^P$-cal) according to an embodiment of the present invention.

DETAILED DESCRIPTION

Figure 1:
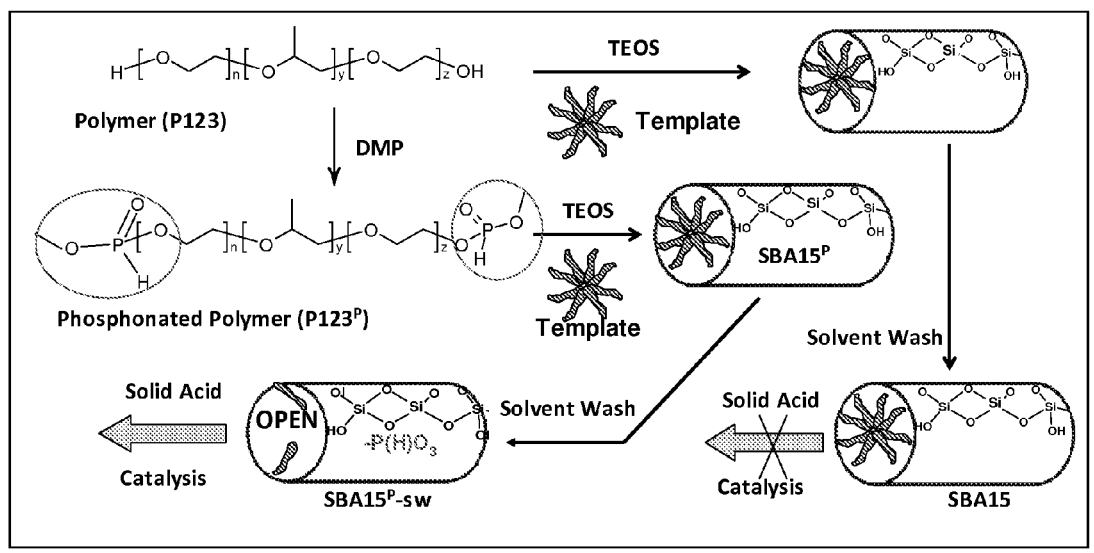
FIG. 1 is a schematic illustration showing the synthesis of hexagonal mesoporous material and solid acid catalyst with solvent extractable phosphonated poloxamer template, P123$^P$ according to an embodiment of the present invention.

The present invention will be more fully understood and appreciated by reading the following Detailed Description in conjunction with the accompanying drawings, wherein like reference numerals refer to like components.

As shown and described herein, in accordance with an embodiment of the present invention, a new and simple synthetic method to produce mesoporous silica and nanoporous solid acid catalysts in one-pot by preparing solvent washable phosphonated triblock copolymer templates and self-assembling them in the presence of alkoxysilanes is provided. New phosphonated poloxamer templates have been designed and synthesized, and are also provided. These phosphonated poloxamer templates have enabled production of a highly ordered mesoporous material with high surface area and pore volume, and also enabled the placement of the cleaved functional phosphonic acid groups in the materials in one-pot resulting in a solid acid nanocatalyst. The potential of the materials as a solid acid catalyst is demonstrated (as described below) in a pinacole-pinacolone rearrangement reaction, which afforded a complete conversion of pinacole to pinacolone. The phosphonated triblock copolymer and the mesoporous material and its catalytic property were characterized by $^1$H and $^{13}$P NMR spectroscopy, transmission electron microscopy, powder X-ray diffraction, small-angle X-ray scattering, size exclusion chromatography, elemental analysis, thermogravimetric analysis, FT-IR spectroscopy, and gas adsorption.

As discussed below in the Examples section, the synthesis of SBA-type mesoporous material and solid acid nanostructures by using phosphonated Pluronic P123 (designated P123$^P$), as a solvent-extractable template is described. As shown in FIG. 1, the synthesis of hexagonal mesoporous material and solid acid catalyst with solvent extractable phosphonated Pluronic template, P123$^P$ is illustrated.

Advantages of the invention are illustrated by the following Examples. However, the particular materials and amounts thereof recited in these examples, as well as other conditions and details, are to be interpreted to apply broadly in the art and should not be construed to unduly restrict or limit the invention in any way.

Materials and Reagents

The following materials and reagents were used in the following Examples. Poly(ethylene glycol)-block-poly(propylene glycol)-block-poly(ethylene glycol) with number-average molecular weight 5,800 g/mol (Pluronics-123 or P123), and tetraethyl orthosilicate (TEOS) were obtained from Sigma-Aldrich. Dimethyl phosphite (DMP) was purchased from Fluka. Hydrochloric acid (12 M), absolute anhydrous ethyl alcohol, 200 proof, acetone, methanol, and diethyl ether, and toluene were obtained from Fisher Scientific.

EXAMPLES

Example 1

Synthesis of Phosphonated Tri-Block P123 Copolymer (P123$^P$)

This Example describes the synthesis of acid cleavable, phosphonated triblock copolymer (P123$^P$) template containing terminal phosphate ester groups by converting the terminal hydroxyl groups of the poly(ethylene glycol) (PEG) blocks of Pluronic P123 or poly(ethylene oxide)-block-poly (propylene oxide)-block-poly(ethylene oxide) triblock copolymer with dimethylphosphite (DMP) using a method reported by Gitsov and co-workers. See (a) Troev, K.; Tsatcheva, I.; Georgieva, R.; Gitsov, I. *J. Polym. Sci., Part A* 2007, 45, 1349-1363. (b) Georgieva, R.; Tsevi, R.; Kossev, K.; Kusheva, R.; Balgjiska, M.; Petrova, R.; Tenchova, V.; Gitsov, I.; Troev K. *J Med. Chem.* 2002, 45, 5797. (c) Gitsov, I.; Johnson, F. E. *J. Poly. Sci., Part A* 2008, 46, 4130-4139.

In brief, 5.0 g of P123 and 100 mL of DMP were mixed in a 250 mL three-necked flask equipped with a magnetic stirrer and attached to a condenser and refluxed at 150° C. under nitrogen for 4 h. Using a condensation trap, the methanol produced in the reaction was removed. The removal of methanol was also measured to show the progression of the reaction. After the reaction and distillation, the mixture was cooled under nitrogen to room temperature and the unreacted DMP was removed using vacuum, producing a waxy residue of phosphonated Pluronic (P123$^P$) triblock copolymer.

Figure 2:
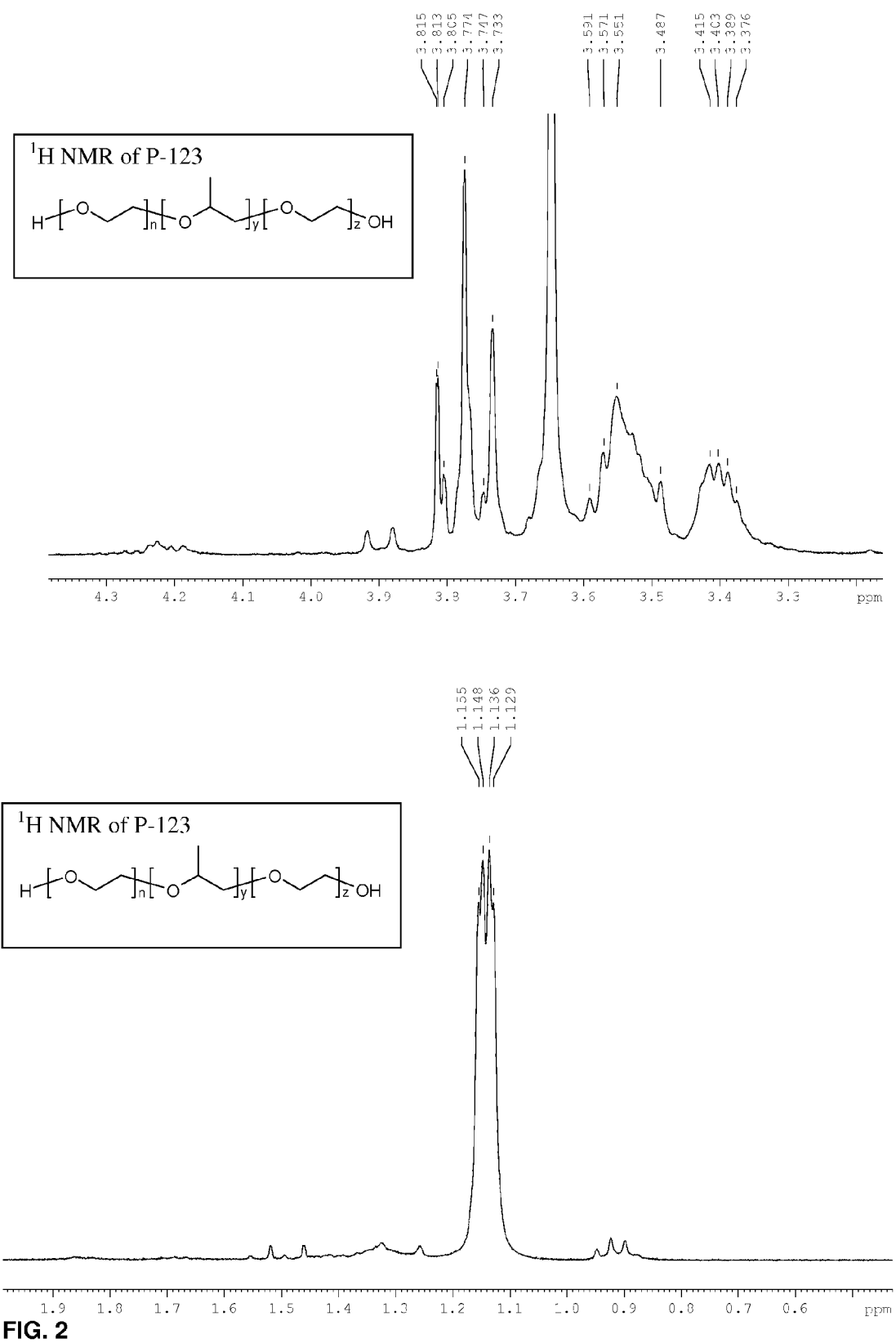
FIG. 2 is a graphical illustration showing $^1$H NMR spectra of non-phosphonated Pluronic P123 triblock copolymer template, according to an embodiment of the present invention.
Figure 3:
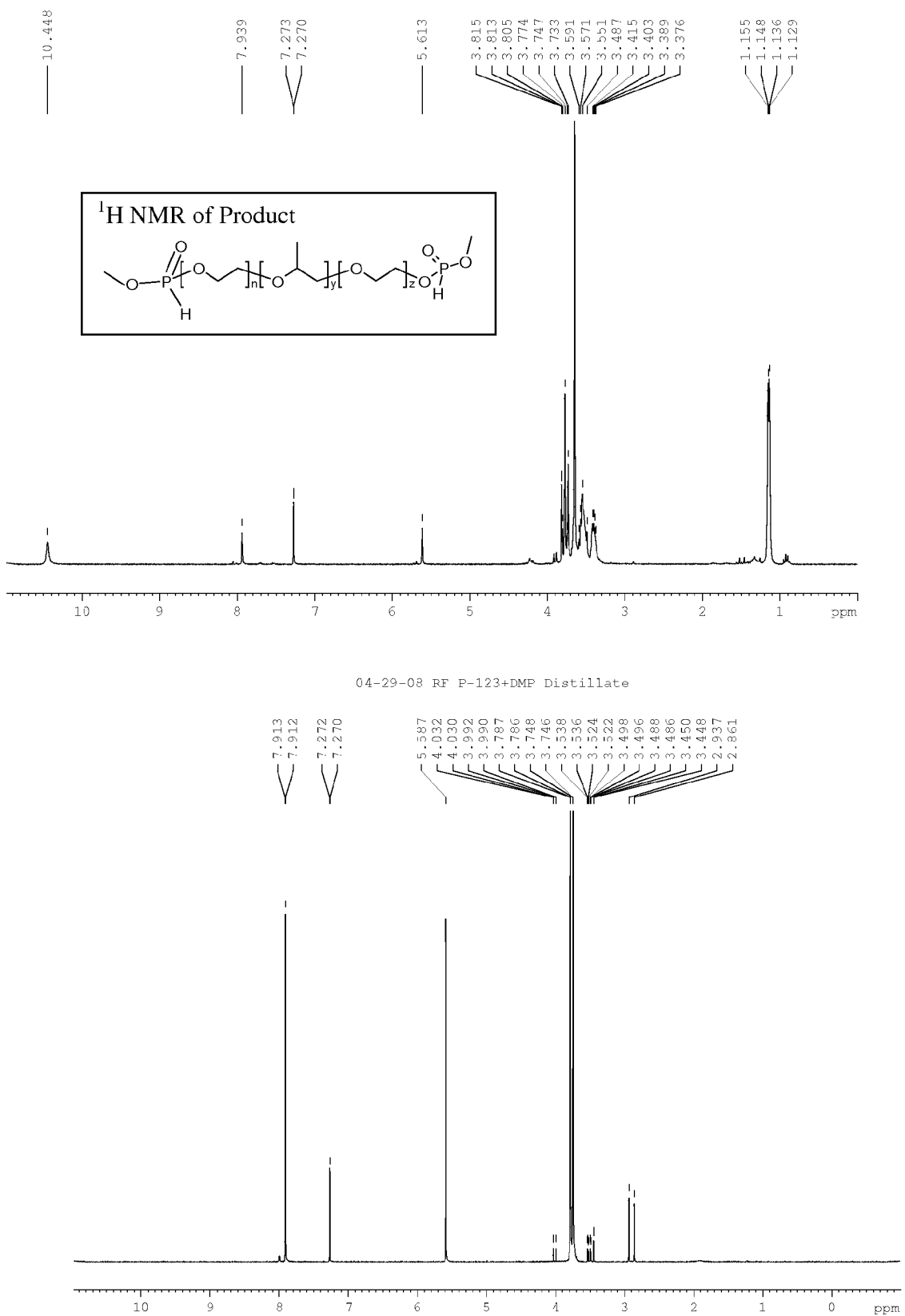
FIG. 3 is a graphical illustration showing $^1$H NMR spectra of phosphonated Pluronic P123$^P$ triblock copolymer template according to an embodiment of the present invention.
Figure 4:
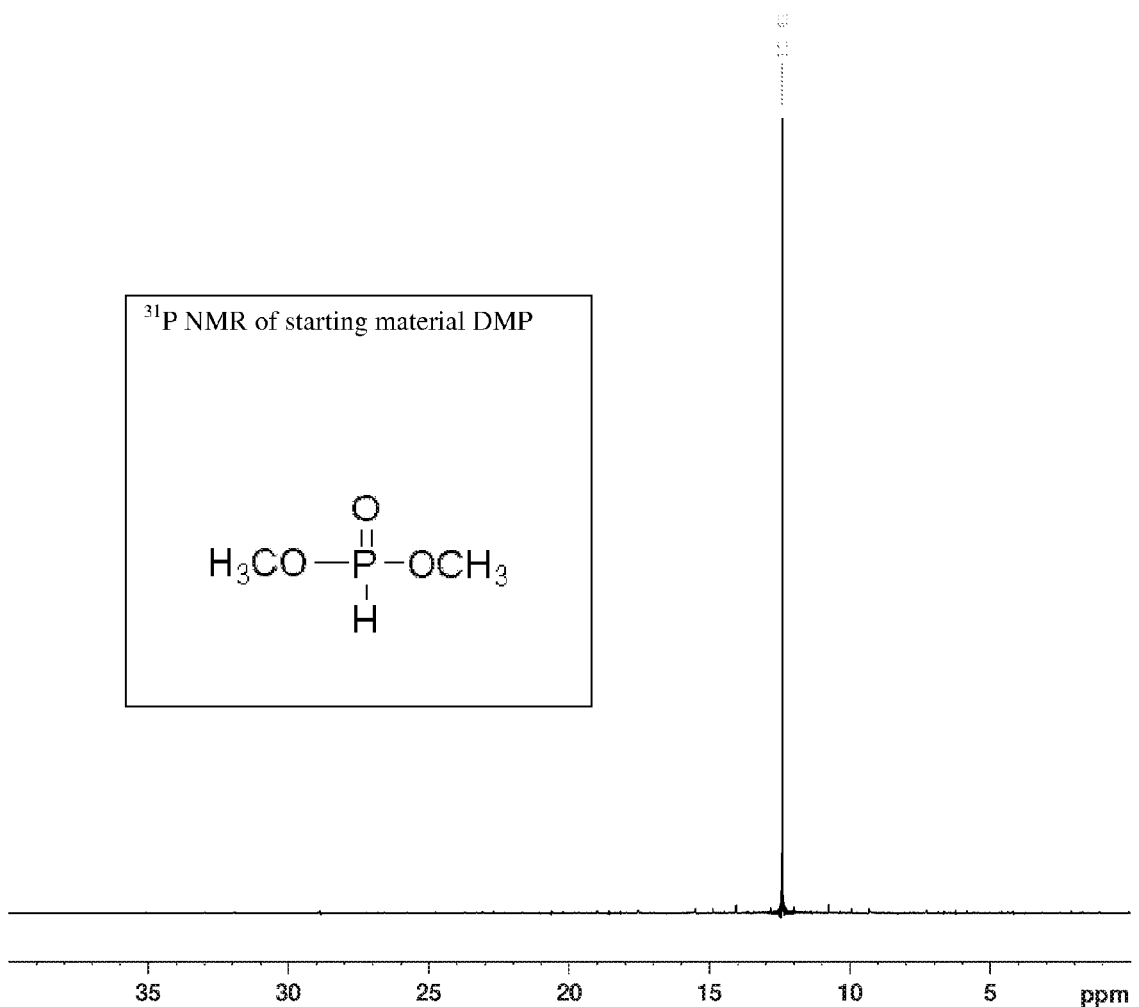
FIG. 4 is a graphical illustration showing $^{31}$P NMR spectrum dimethyl phosphite, DMP according to an embodiment of the present invention.
Figure 5:
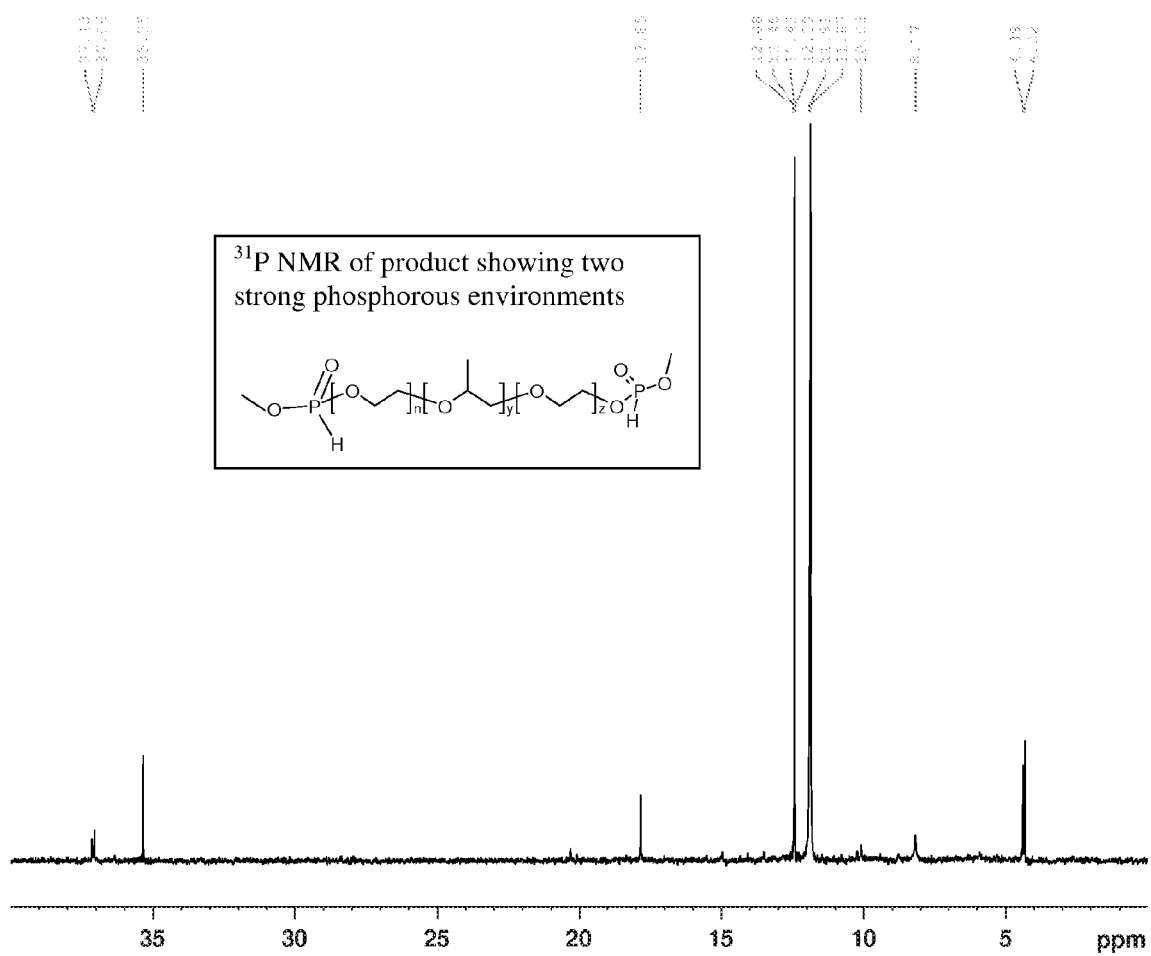
FIG. 5 is a graphical illustration showing $^{31}$P NMR spectrum phosphonated Pluronic, P123$^P$ according to an embodiment of the present invention.
Figure 6:
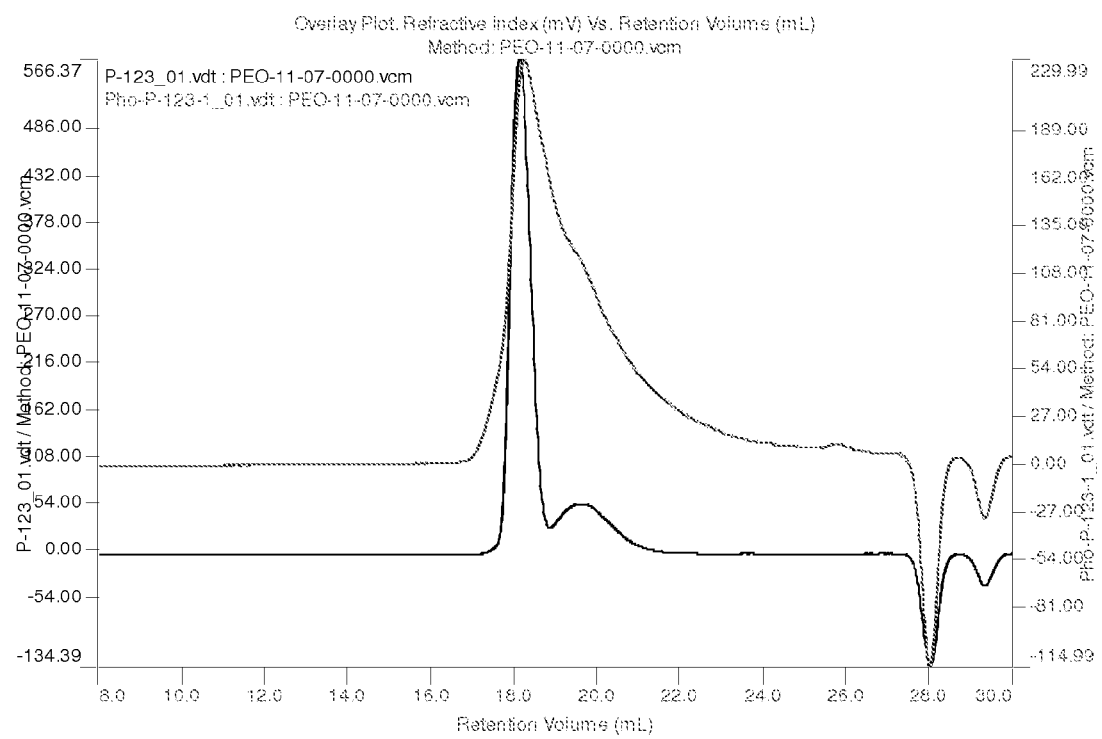
FIG. 6 is a graphical illustration showing size exclusion chromatography (SEC) of P123 and P123$^P$ (or P123 after phosphorylation) according to an embodiment of the present invention.

The synthesis of the phosphonated Pluronic template, P123$^P$, was proved by $^1$H and $^{31}$P NMR spectroscopy (see FIGS. 2-5) and gel permeation chromatography (GPC) (FIG. 6) ($^1$H NMR (CDCl3): δ6.75 (d, $^1$J(P,H)=710.12 Hz, CH$_3$OP (O)(H)O—); 4.03 (—OP(O)(H)OCH$_2$), 4.03 (—OP(O)(H) OCH$_3$), and 3.47-3.60 (m, —OCH$_2$CH$_2$O—). $^{31}$P NMR (CDCl$_3$): δ11.87-11.91 (m, —CH$_2$OP(O)(H)OCH$_3$) and 12.45 (m, residual DMP, CH$_3$OP(O)(H)OCH$_3$)). In particular, FIG. 2 shows $^1$H NMR spectra of Pluronic P123 triblock copolymer template; FIG. 3 shows $^1$H NMR spectra of phosphonated Pluronics, P123$^P$ triblock copolymer template; FIG. 4 shows $^{31}$P NMR spectrum dimethyl phosphite, DMP; and FIG. 5 shows $^{31}$P NMR spectrum of phosphonated Pluronic, P123$^P$. FIG. 6 shows size exclusion chromatography (SEC) of P123 (in black color) and P123$^P$ (or P123 after phosphorylation) (in green color). The (black) lower trace is for the starting P-123, which has two fractions with different molecular weights, the right one being of lower molecular weight. The (green) upper trace is the phosphorylated derivative and it is obvious that some chemical transformation has occurred on it, since the shape is different. Based on previous reports of analogous samples and based on the elution time of the sample as well as the signals as shown in the NMR spectra, a substantial part of the original P123 polymer is indeed phosphorylated.

The results show that the $^1$H NMR spectra after the reaction between P123 and dimethylphosphite (DMP) has a doublet centered at δ6.75 (d, $^1$J(P,H)=710.12) corresponding to CH$_3$OP(O)(H)O—. Furthermore, peaks at δ4.03 corresponding to —OP(O)(H)OCH$_2$— and —OP(O)(H)OCH$_3$), and 3.47-3.60 (m, —OCH$_2$CH$_2$O—) are observed. A peak at 4.01 is missing on the spectrum for P123. This strongly supports the addition of phosphate ester group to the terminal ends of the PEG of the P123 triblock copolymer. Additionally, the $^{31}$P NMR spectrum shows δ11.87-11.91 corresponding to —CH$_2$OP(O)(H)OCH$_3$ and 12.45 corresponding to residual DMP, CH$_3$OP(O)(H)OCH$_3$). The signal at 11.87-11.91 is generated by phosphorous groups attached to the ends of the P123$^P$ tri-block copolymer. Both the $^1$H and $^{31}$P confirmed the exchange of terminal OH groups in the PEO template of P123 to phosphate groups. The latter is further confirmed by running the $^{31}$P NMR of pure DMP, which shows a peak at ~12.41 ppm.

Example 2

Synthesis of Mesostructured Silica

This Example describes the self-assembly of the resulting P123$^P$ polymer with tetraethoxysilane (TEOS) in aqueous solution to produce phosphonated mesostructured silica, SBA15$^P$, under conditions similar to those reported for making SBA15 with P123. The synthesis of SBA15 with P123 was reported previously by Stucky and co-workers Zhao, D.; Feng, J.; Huo, Q.; Melosh, N.; Fredrickson, G. H.; Chmelka, B. F.; Stucky, G. D. *Science* 1998, 279, 548-551).

Synthesis of Mesoporous Silica with Phosphonated Pluronics, P123$^P$

In brief, SBA15$^P$ mesoporous material was synthesized by following the procedure reported by Stucky et al. (Zhao, D.; Feng, J.; Huo, Q.; Melosh, N.; Fredrickson, G. H.; Chmelka, B. F.; Stucky, G. D. *Science* 1998, 279, 548-551) but by using the novel phosphonated Pluronic, P123$^P$, template as described herein. Typically, 4.15 g of the P123$^P$ template was mixed into and 200.0 mL distilled water under stirring. Upon complete dissolution of the triblock copolymer, 40.0 mL, 12 M HCl and 18.22 g of tetraethyl orthosilicate (TEOS) were added and the reaction mixture was stirred at 40° C. for 20 h. Then the material was aged for 24 h at 80° C. The solution was filtered and the solid product was dried at 90° C. for 24 h. This produced the sample labeled as-synthesized mesostructured material, SBA15$^P$.

Synthesis of Mesoporous Silica SBA-15 with Pluronics, P123

As a control sample, SBA-15 (or labeled here as SBA15), was prepared by following the procedure reported by Stucky and co-workers (Zhao, D.; Feng, J.; Huo, Q.; Melosh, N.; Fredrickson, G. H.; Chmelka, B. F.; Stucky, G. D. *Science* 1998, 279, 548-551). Typically, 4.15 g of the P123 template was mixed with 40.0 mL, 12 M HCl and 200.0 mL distilled water. Upon complete dissolution of the triblock copolymer, 18.22 g of tetraethyl orthosilicate (TEOS) was added and the reaction mixture was stirred at 40° C. for 20 h. Then the material was aged for 24 h at 80° C. The solution was filtered and the solid product was washed with copious amount of water and dried at 90° C. for 24 h. This produced the sample labeled as-synthesized mesostructured material, SBA-15 (also denoted here as SBA15).

Example 3

Extraction of Template

This Example describes template extraction which was performed under various conditions with special attention to solvent extraction with the expectation that P123$^P$ template will be easily removed through a low temperature solvent washing by undergoing hydrolysis at its terminal phosphate ester groups. For comparison purposes, a material templated with as-received P123 or the SBA15 described above subjected to similar extraction conditions.

Briefly, solvent washing and calcination is described herein.

Solvent Washing 1.0 g of the mesostructured material, SBA15$^P$ or SBA15, synthesized above was stirred in a 1:1:1 ratio of acetone, ethanol and diethyl ether at 50° C. for 24 h followed by 3 washes with 20 mL of ethanol and then filtered and dried for 24 h at 80° C. The resulting solvent washed mesoporous materials synthesized from P123$^P$ and P123 were labeled as SBA15$^P$-sw and SBA15-sw, respectively.

Calcination 1.0 g of the mesostructured material, SBA15$^P$ or SBA15, was kept on a quartz boat in a quartz cylinder inside a furnace and heated at a ramp of 2.0° C./min at 600° C. for 24 h under air. Then the heat was ramped down at a rate of 2.0° C./min until the furnace reached room temperature. This resulted in calcined samples, SBA15$^P$-cal and SBA15-cal, respectively.

Example 4

Characterization

This Example describes the characterization of the samples of Example 3 with small angle X-ray scattering (SAXS), transmission electron microscopy (TEM), gas adsorption, powder X-ray diffraction (XRD), elemental analysis, thermogravimetric analysis and solid-state NMR and FT-IR spectroscopy (FTIR).

Small Angle X-ray Scattering (SAXS), XRD Patterns, and TEM Images

Figure 7:
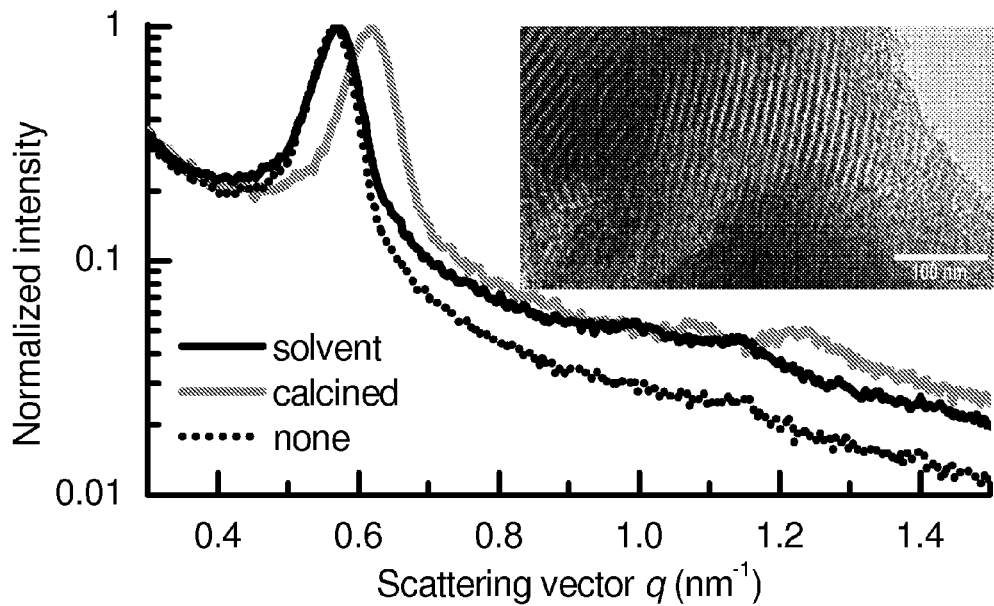
FIG. 7 is a graphical illustration showing small angle X-ray scattering (SAXS) of mesoporous silica as synthesized from phosphonated template, P123$^P$ (SBA15$^P$) and following solvent washing (SBA15$^P$-sw) and calcination (SBA15$^P$-cal), and also showing in an inset: transmission electron micrograph (TEM) of SBA15$^P$-sw, according to an embodiment of the present invention.

FIG. 7 shows small angle X-ray scattering (SAXS) for material made with P123$^P$ in its as-synthesized state (SBA15$^P$), after solvent washing (SBA15$^P$-sw), and after calcination (SBA15$^P$-cal). The results show that all three samples yield a peak near 0.6 nm$^{-1}$; higher order peaks are also discernible. The scattering for sample SBA15$^P$-sw is similar to that of SBA15$^P$, which supports the idea that the gentler approach of solvent extraction will not change the mesostructure. SBA15$^P$-cal showed a slight unit cell shrinkage indicating that high temperature calcination reduced the unit cell of the material. The XRD patterns also exhibited that the materials have ordered mesostructures with unit cell dimensions of 11.5, 11.5, and 10.3 nm for SBA15$^P$, SBA15$^P$-sw, and SBA15$^P$-cal, respectively. The TEM images, as shown in FIG. 7, are consistent with a hexagonally ordered mesostructure.

Gas Adsorption and Thermogravimetric Analysis (TGA)

Solution phase $^1$H-NMR spectra was measured with a Bruker DPX-300 MHz spectrometer using CDCl$_3$. Solution phase $^{31}$P NMR spectra was measured using a Bruker DRX-500 MHz spectrometer. Thermogravimetric analysis (TGA) traces were recorded using Q500 thermogravimetric analyzer (TA Instruments) with temperature ramp at 10° C./min under air flow. The nitrogen adsorption isotherms, surface area and pore size distributions were measured with a Micromeritics Tri-Star 3000 surface area and porosity analyzer. The data was calculated by using the Burunauer-Emmett-Teller (BET) and Barrett-Joyner-Halenda (BJH) methods. The transition electron micrographs were taken using the FEI Tecnai T-12 transition electron microscope.

Figure 8:
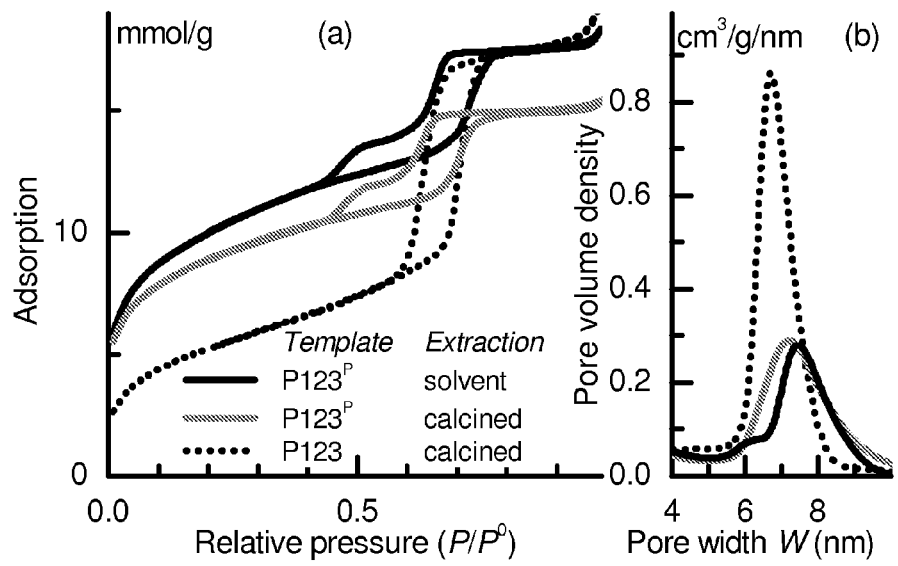
FIG. 8 is a graphical illustration showing (a) nitrogen gas adsorption/desorption isotherms and (b) pore volume distribution of SBA15$^P$ (from P123$^P$) and SBA15 (from P123) after template extraction with solvent washing and calcination, according to an embodiment of the present invention.

FIG. 8(a) illustrates nitrogen gas adsorption isotherms for several template-extracted samples; the results show that they all have type IV isotherms, which is indicative of the presence of mesoporous structures in the materials. Compared with SBA15, the results regarding the samples prepared from P123$^P$ (or sample SBA15$^P$), showed two desorption steps indicating that they have bottle-neck shaped pores or pore clogging. This may be due to the presence of residual phosphate ester groups on the walls of the materials after solvent washing or possible residues of phosphorus oxides from oxidation of phosphate esters inside the mesopores upon calcination. The pore size distribution shown in FIG. 8(b) that was calculated from the isotherms, revealed that sample SBA15$^P$-sw, SBA15$^P$-cal and SBA15$^P$ have major pore diameters of 8.5, 8.5, and 8.0 nm, respectively. It is worth noting that SBA-15 showed insignificant complementary or interconnecting small pores with only 0.09 cc/g pore volume, while samples synthesized with P123$^P$ showed significant amount of such pores with an average size of 2.8 nm and with >0.2 cc/g pore volume (see FIG. 9; and Table 1, below). FIG. 9 is a graphical illustration showing pore size distribution of template extracted samples (A) SBA15$^P$-sw, (B) SBA15$^P$-cal, and (C) SBA15. Table 1, below, shows structural data of mesoporous materials.

TABLE 1

| Sample | Surface Area (m$^2$/g)$^a$ | Pore Volume (cm$^3$/g)$^b$ | Pore Volume (cm$^3$/g)$^c$ | Major Pore Diameter (nm)$^d$ | Small Pore Diameter (nm)$^e$ | Unit Cell (nm)$^f$ |
|---|---|---|---|---|---|---|
| SBA15$^P$-sw | 804 | 0.63 | 0.27 | 8.53 | 2.28 | 11.5 |
| SBA15$^P$-cal | 717 | 0.53 | 0.21 | 8.52 | 2.28 | 10.3 |
| SBA15-sw | 428 | 0.68 | 0.09 | 7.97 | NA | 8.90 |

$^a$BET surface area calculated from 0.05-0.2 range.
$^b$Single-point pore volume (total volume of small pores, primary mesopores and some textural porosity).
$^c$Pore volume of pores below 6 nm for interconnecting and complementary pores calculated by integration of pore size distribution up to 6 nm.
$^d$Pore diameter calculated with KJS method.
$^e$Maximum of small, complementary pores.
$^f$Unit cell calculated with P6 mm hexagonal structure with a$_o$ = 2d$_{100}$/3$^{1/2}$ (Å).

Figure 10:
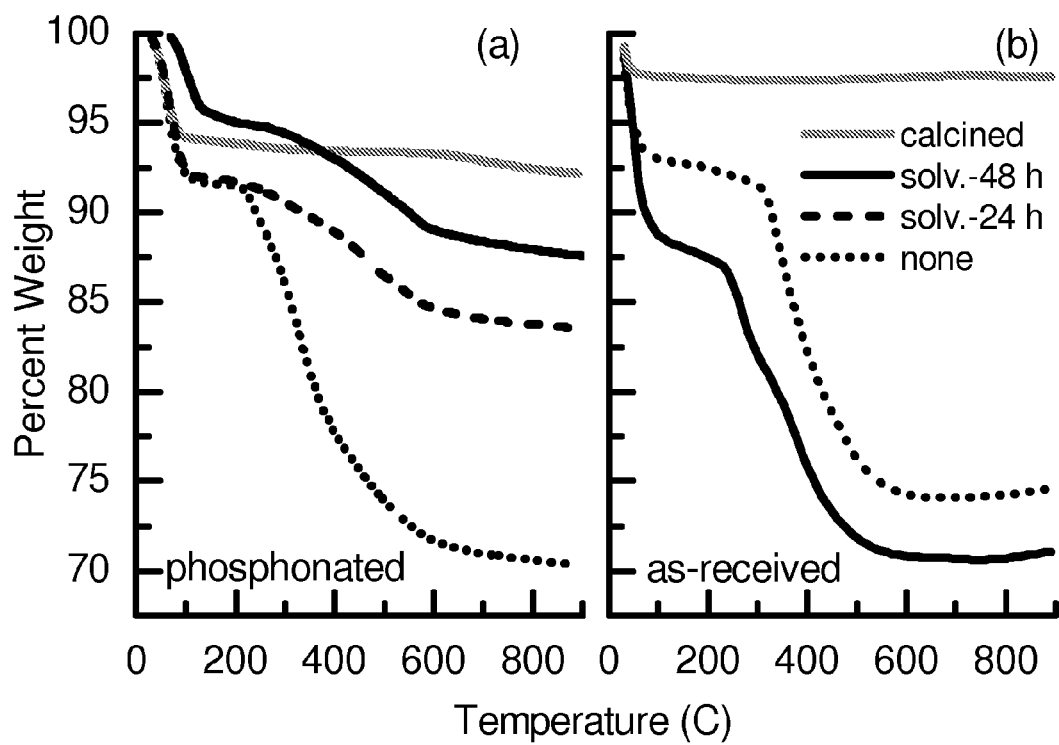
FIG. 10 is a graphical illustration showing thermogravimetric traces before and after solvent washing of mesoporous materials made with (a) P123$^P$ and (b) as-received P123, according to an embodiment of the present invention.

The thermogravimetric analysis (TGA) traces (FIG. 10) for the mesoporous samples show two step downs. In the first ~25-100° C., the results show a distinct drop in weight is observed which is attributed to evaporation of physisorbed water. In the second drop between ~200° C.-600° C., the results show another distinct weight loss due to the oxidation of the organic template. Upon comparing the graphs in FIG. 10a (mesoporous samples made using the new P123$^P$ template) to graphs in FIG. 10b (P123 template), a significant difference particularly between the two different solvent washes was observed. For the samples synthesized from P123$^P$, the calculated difference between the weight losses in the range of ~200° C.-600° C. for unextracted material and solvent washed for 24 h was 14%; when extracted for 48 h, an additional weight loss of 6% was observed (FIG. 10a). For the SBA15 sample synthesized from P123, the solvent washed sample lost only about 3% mass compared to the untreated sample. This clearly indicates that a simple solvent washing that is unable to remove P123 template does remove most of the mass of P123$^P$ template. The greater weight loss in sample SBA15$^P$ is attributed to the hydrolytic cleavage of terminal phosphate ester groups of P123$^P$, helping the removal of the bulk of the template leaving residual phosphate or phosphonic acid groups intact on the walls of the material.

FT-IR Spectral Analysis of the Samples

To confirm the presence of the phosphate ester or phosphonic acid groups in the SBA15$^P$, the sample was characterized with elemental analysis and FT-IR spectroscopy. FT-IR spectra were obtained with Nicolet 6700 FT-IR Spectrometer. In brief, after solvent washing and calcination, the SBA15 and SBA15$^P$ were also characterized by FT-IR spectroscopy (FIG. 11). The results showed the presence of residual phosphorus and phosphates after solvent washing in sample SBA15$^P$. Most of the phosphate ester groups of the P123$^P$ survive the self-assembly process as cleavage of phosphate esters may occur only after several minutes, if any, during self-assembly at low pH.

The FT-IR spectra results of all the mesoporous samples show three peaks at 452-457, 797, and 1070 cm$^{-1}$ corresponding to rocking, bending (or symmetric stretching), and asymmetric stretching of the tetrahedral oxygen atoms in the SiO$_2$ structure or Si—O—Si framework. A peak at 950 cm$^{-1}$ can be assigned to the asymmetric stretching of silanol, Si—OH, as well as P—OH groups and P—O—P units. This peak was slightly broader on the spectrum of sample SBA15$^P$-sw compared to that of SBA15-sw indicating that the peak may also contain the asymmetric stretching vibrations of P—OH groups and P—O—P units in the latter. The corresponding peak on the spectrum for SBA15$^P$-cal is prominent and shifted to 975 cm$^{-1}$ compared to that of SBA15$^P$-sw, indicating that most of the P—OH groups may have been condensed into P—O—Si unites in the former. Additionally, this peak is not observed on the spectrum for SBA15-sw. The peak at 820 cm$^{-1}$ was also observed only on the spectrum of the calcined SBA15$^P$-cal sample, which corresponds to symmetric stretching of P—O—Si and P—O—P units.

More interestingly, the FTIR spectra of the samples made from phosphonated template exhibited more or stronger peaks in the region of 1150-1300 cm$^{-1}$ compared to the spectra of the samples made from non-phosphoanted Pluronic template. These new peaks are stronger on the spectrum of SBA15$^P$-cal compared to that of SBA15$^P$. On the other hand, the FT-IR spectra indicated that the band at 1070 cm$^{-1}$ becomes almost unchanged for the SBA15-cal sample compared to SBA15. These new absorption bands between 1150-1300 cm$^{-1}$ are related to vibration modes of P=O bonds or different PO$_x$ metaphosphate units. Particularly peaks at 1190 and 1255 cm$^{-1}$ in the spectrum of SBA15$^P$-cal, which are very visible in SBA15$^P$-cal, correspond to symmetric stretching vibrations of the metaphosphate units and asymmetric stretching modes of P=O bonds, respectively. Upon heat treatment, the positions of these peaks are known to change progressively to higher wave numbers. The new peak on 544 cm$^{-1}$ on the spectrum SBA15$^P$-cal can be assigned to assigned to harmonic bending vibration of O'P—O linkages.

Besides its ease of extraction by hydrolytic cleavage, the use of P123$^P$ template allowed the placement of residual phosphate ester and phosphonic acid groups on the mesoporous framework, creating a solid acid nanocatalyst in one-pot.

Example 5

Solid-Acid Catalyzed Pinacole-Pinacolone Rearrangement Reaction by Using Phosphonic Acid Functionalized Mesoporous Catalyst This Example describes testing of the material by acidifying its phosphate esters with dilute HCl solution and then using the resulting material as a solid acid catalyst in the pinacole-pinacolone rearrangement reaction. The results show that the acidified SBA15$^P$ material showed nearly a 100% conversion of the reaction compared to a 0% conversion for its acidified SBA15 counterpart.

Briefly, a solid acid catalyzed pinacole-pinacolone reaction was conducted by using the mesoporous material, SBA15$^P$-sw, as a catalyst. Typically, 6.0 g of pinacol was mixed with 0.2 g SBA15$^P$-sw catalyst and stirred at 140° C. with no solvent. Control experiment using SBA15 as a catalyst was also conducted in the same way. The reaction mixture was taken with a filter syringe and characterized by $^1$H NMR spectroscopy.

Figure 12A:
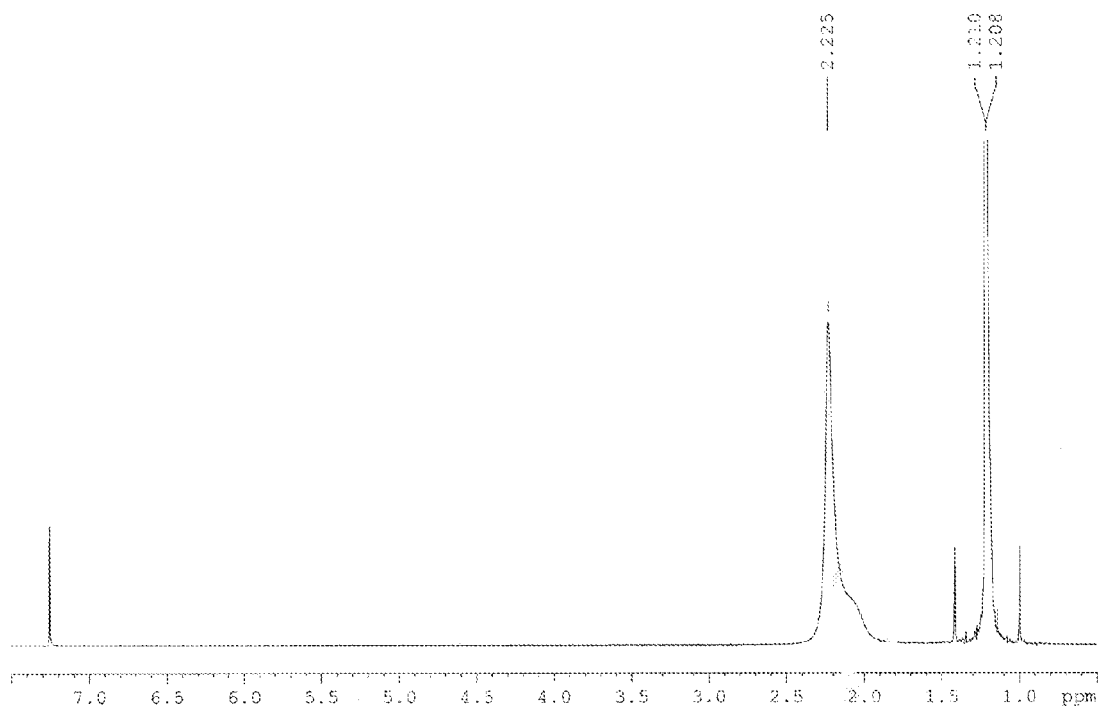
FIG. 12 is a graphical illustration showing $^{31}$H NMR spectra of a reaction mixture of a pinacole-pinacolone rearrangement reaction catalyzed by mesoporous catalysts synthesized from (a) P123 and (b) P123$^P$; and (c) NMR spectrum of a pure reactant, pinacol according to an embodiment of the present invention.
Figure 12B:
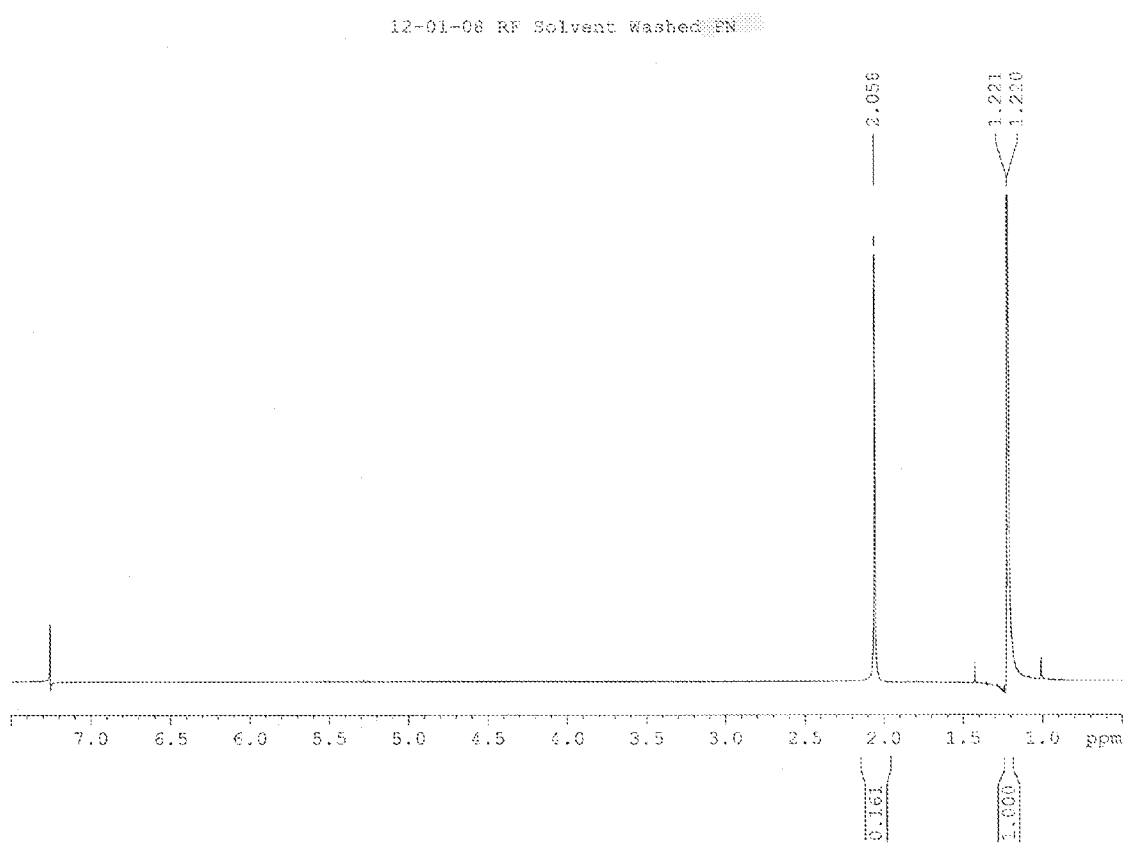
Figure 12C:
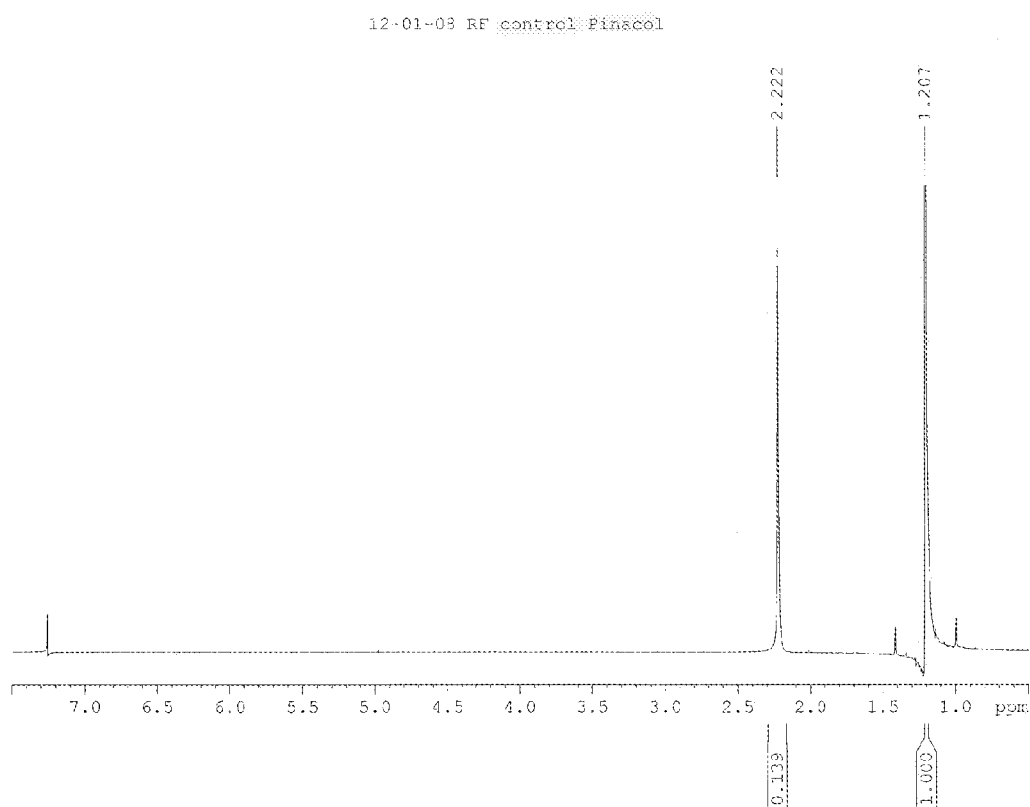

The $^1$H NMR spectra of the reaction mixture clearly show that the material synthesized from the phosphonated template after solvent washing, SBA15$^P$, display solid acid catalytic property for the pinacole-pinacolone transformation as observed from the peaks at chemical shifts of 2.06 and 1.21 ppm that correspond to CH$_3$—C(=O) and CH$_3$—C protons of the pinacolone, respectively. On the other hand, the solvent washed SBA15 did not catalyze the reaction as observed from the peaks at 2.22 and 1.21 ppm corresponding to CH$_3$—C and C—OH protons of pinacole, respectively. This was further confirmed by comparing to the NMR spectrum of the starting pincol (FIG. 12c) and the NMR data for pinacole and pinacolone on Sigma-Aldrich catalogue.

The results of the above described Examples show synthesized mesoporous silica by preparing and using a phosphonated template, P123$^P$, and demonstrated its extraction by a simple solvent washing. Similar solvent washing procedures including soxhlet extraction (Liang, Y.; Hanzlik, M.; Anwander, R. Chem. Commun. 2005, 525-526; Leventis, N.; Mulik, S.; Wang, X.; Dass, A.; Patil, V. U.; Sotiriou-Leventis, C.; Lu, H.; Churu, G.; Capecelatro, A. J. Non-Cryst. Solids 2008, 354, 632-644), stirring in supercritical fluids (Zhang, W.-H.; Lu, X.-B.; Xiu, J.-H.; Hua, Z.-L.; Zhang, L.-X.; Robertson, M.; Shi, J.-L.; Yan, D.-S.; Holmes, J. D. Adv. Funct. Mater. 2004, 14, 544-552), and stirring under reflux conditions (Wang, X.; Lin, K. S. K.; Chan, J. C. C.; Cheng, S. J. Phys. Chem. B 2005, 109, 1763-1769) are unable to remove the P123 template as much. The residual phosphate ester groups were shown to be converted into phosphonic acids, making the material a solid acid nanocatalyst; its catalytic activity was demonstrated by acid-catalyzed pinacole to pinacolone transformation.

The following Example describes the preparation of a DSSC, according to an embodiment of the present invention, which uses a solvent-washed, templated-mesoporous metal oxide, preferably a solvent-washed, templated-mesoporous $TiO_2$ as an electrode.

Example 6

Transesterification Reaction by Using Phosphonic Acid Functionalized Mesoporous Catalyst Similarly to Example 5 above, the mesoporous material, SBA15$^P$-sw, was used as a catalyst in a transesterification reaction.

SBA15$^P$-sw was successfully used as a catalyst for esterification reaction of acetic acid with ethanol. The catalyst produced 40% conversion with 100% selectivity to ethyl acetate at 75° C. in 24 h whereas in a control run only 25% conversion in the same time was observed. Also this catalyst was successfully recycled 5 times with only marginal loss in activity. This slight loss in activity was mainly due to handling losses of catalyst. These experiments suggest that an important catalyst has been generated.

It is contemplated by the present invention that this catalyst (and similar material discussed herein) can be used as a catalyst for other acid-catalyzed reactions.

Example 7

DSSC Using a Solvent Washed, Templated-Mesoporous Metal Oxide

Figure 13A:
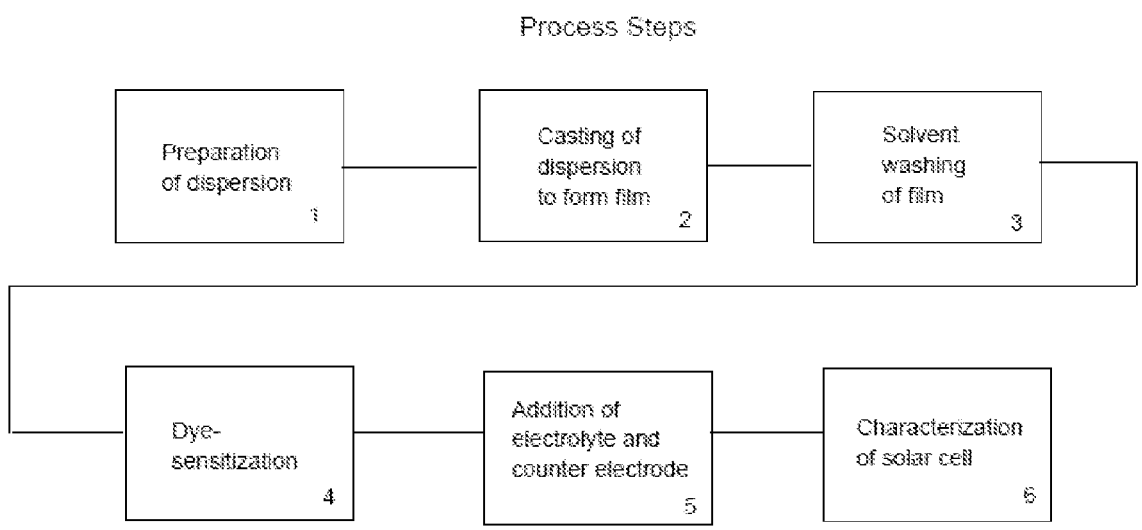
FIG. 13a shows the steps in a process to prepare and characterize a DSSC, according to an embodiment of the present invention.
Figure 13B:
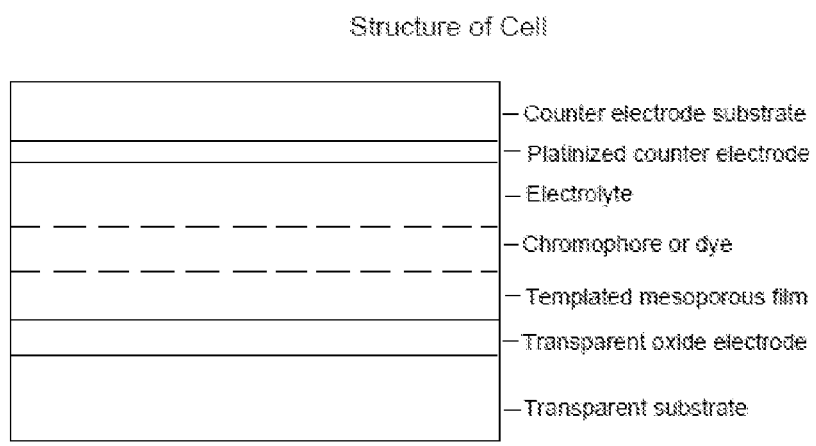
FIG. 13b shows the structure of a DSSC, according to an embodiment of the present invention.
Figure 13C:
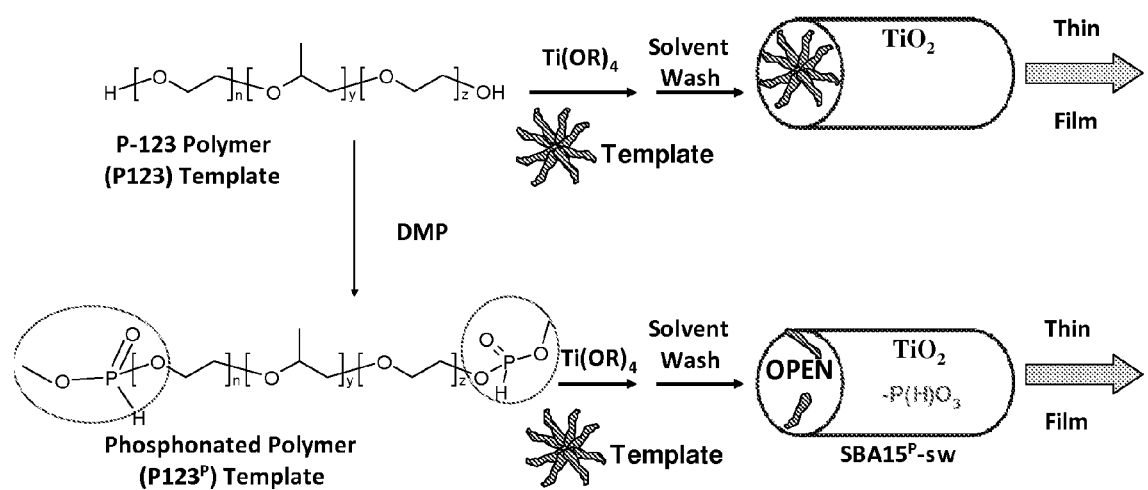
FIG. 13c shows the synthetic process to form mesoporous titania by self-assembly of phosphonated poloxamers with Ti(OR)$_4$, for use in a solar cell (e.g., a DSSC), according to an embodiment of the present invention.

The process steps performed to prepare and characterize a DSSC, which uses a solvent-washed, templated-mesoporous metal oxide, preferably a solvent-washed, templated-mesoporous $TiO_2$ as an electrode, are discussed herein. These steps are generally illustrated in FIG. 13a, and include but are not limited to (1) preparation of a dispersion (after the preparation of a phosphonated template) containing a sol-gel solution of phosphonated Pluronics (P123$^P$) and Ti(OR)$_4$ such as titanium(IV) ethoxide, (2) casting of the dispersion to form a film, (3) solvent washing of the film, (4) dye-sensitization; (5) addition of electrolyte and counter electrode; and (6) characterization of the solar cell. FIG. 13b shows the structure of a DSSC, according to an embodiment of the present invention. This structure is different from conventional DSSCs based on sintering of particles at high temperatures to form a mesoporous film. This structure also differs from DSSCs based on templated SBA-type mesoporous metal oxide films in which the templating molecule is removed by high-temperature calcination (See M. Nedelcu, J. Lee, E. J. W. Crossland, S. C Warren, M. C. Orilall, S. Guldin, S. Huettner, C. Ducati, D. Eder, U. Wiesner, U. Steiner, and H. J. Snaith, *Soft Matter* 5, 134-139 (2009)). FIG. 13c shows the synthetic process to form mesoporous titania by self-assembly of phosphonated poloxamers with Ti(OR)$_4$, for use in a solar cell (e.g., a DSSC), according to an embodiment of the present invention.

Preparation of Phosphonated Template

In the first step of synthesis, a commercially obtained poloxamer molecule (BASF Corp. "Pluronic P123"), which is a nonionic, triblock copolymer consisting of a central chain of polyoxypropylene flanked by two identical chains of polyoxyethylene, as discussed above, was phosphonated. Phosphonation was done by mixing 5.0 g of P123 and 100 mL of dimethylphosphite (DMP) in a 250 mL round bottomed flask. The flask was attached to a distiller apparatus, and was heated to 150° C. under nitrogen while stirring for a 4 h distillation period. Using a condensation trap, the production of methanol was measured during this period to monitor the reaction between P123 and DMP. After the distillation period the mixture was cooled to room temperature. The un-reacted DMP was removed from the mixture by vacuum pumping; the waxy residue remaining after pumping is the phosphonated template polymer.

Preparation of Phosphonated-Template/Titania-Precursor Dispersion 1.0 g of phosphonated template polymer (prepared as discussed in the section above) was dissolved in 12.0 g of ethanol in a 100 mL Pyrex beaker at room-temperature. In a second beaker, 3.88 mL of titanium(IV) ethoxide and 2.70 mL of hydrochloric acid (12.0 molar) were mixed for 5.0 min while in an ice bath. While stirring the solution in the second beaker, the solution in the first beaker was transferred into the second and stifling continued for 10 min; an ice-bath was not employed during this aging process.

Casting of Titania/Polymer Films From the Dispersion

Promptly following the aging process (as discussed in the section above), the phosphonated-template/titania-precursor dispersion was cast onto a substrate to form a titania/polymer film. Both dip-casting and spin-casting have been used (any casting as understood by those skilled in the art may be used). For spin casting, the typical conditions used were: (a) 20.0 sec at ~1000 rpm, then (b) 20.0 sec at ~1500 rpm. A typical film thickness obtained by spin-casting was 300 nm. Thicker films were prepared by repeating the casting procedure. Following casting, the coated substrates were heated for 1 h at 80° C. in air.

Solvent-Washing to Form a Titania-Based Film

The titania/polymer films (prepared as discussed in the section discussed above) were solvent washed to remove most of the polymer component. The films and substrates were immersed in a 1:1:1 mixture of diethyl ether, acetone and ethanol in a 250 mL round bottomed flask at 50° C. for 4 hours while stirring the mixture; we used an oil bath to establish the washing temperature. The samples were then air dried and stored in air. Solvent washing creates mesoporous films was confirmed; a typical internal surface area estimated using gas adsorption/desorption measurements and the "BET" analysis was 270 m$^2$ g$^{-1}$. It is expected that the titania has a phosphorus group bonded to its internal surfaces after solvent washing.

Sensitization of Mesoporous Titania Film

Mesoporous titania film was sensitized using a commercially obtained dye solution (acetonitrile/tert-butyl alcohol (50:50 v/v %) containing 3×10$^{-4}$ M Ru[LL'(NCS)$_2$] (L=2,2'-bipyridyl-4,4'-dicarboxylic acid, L'=2,2'-bipyridyl-4,4'-ditetrabutylammoniumcarboxylate)) developed for sensitization of sintered mesoporous titania. The templated mesoporous titania films were soaked in the as-received dye solution for 18 hours at room-temperature. The films were then removed from the dye solution, allowed to dry in air, and then rinsed in ethanol several times. Dye adsorption was confirmed by comparing the optical transmittance spectra of the films before and after soaking in the dye.

Solar Cell Fabrication

The following is a description of the fabrication of a particular type of solar cell using the phosphonated mesoporous titania film (as prepared above) as an electrode in the cell. Additional types of solar cell incorporating a phosphonated mesoporous titania film, but using alternative chromophores and using alternative electrolytes or polymers to electrically contact the counterelectrode, are contemplated by the present invention.

To prepare a solar cell, the substrates on which the titania/polymer films were cast were commercially obtained glass slides with a fluorinated tin oxide (FTO) coating that is electrically conducting. These substrates were modified following a published procedure (See N. Kopidakis, E. A. Schiff, N.-G. Park, J. van de Lagemaat, and A. J. Frank, *J. Phys. Chem. B* 104, 3930-3936 (2000)). The substrates were immersed for 4 hours in hydrogen peroxide $H_2O_2$. A 10 mM solution of Ti(IV) butoxide in 2-propanol was then spin-cast onto the FTO-coating on the substrate (20 sec at 1000 rpm). Thus, the phosphonated titania, as described in this Example, was prepared on top of a thin non-phosphonated titania layer.

The counterelectrode was an FTO-coated glass slide that had been platinized by spreading a drop of 5 mM dihydrogen hexachlororoplatinate(IV) acid (Fluka, purum) in 2-propanol onto the counterelectrode, followed by heating in air at 380° C. for 15 m. A solar cell was completed using the substrate with the FTO/(templated mesoporous titania) structure (prepared as discussed above) as one electrode. Procedures previously developed for preparation of a DSSC using sintered mesoporous titania films were followed. A drop of electrolyte "DMPII" (0.05 M $I_2$, 0.1 M LiI, 0.6M 1-methyl-3,propylimidazolium, 0.5 M 4-tert-butylpyridine in acetonitrile) was cast onto the film. The counterelectrode was placed onto the electrolyte-filled film. The area of the cell was typically 1.0 $cm^2$.

Solar Cell Characterization

Figure 14:
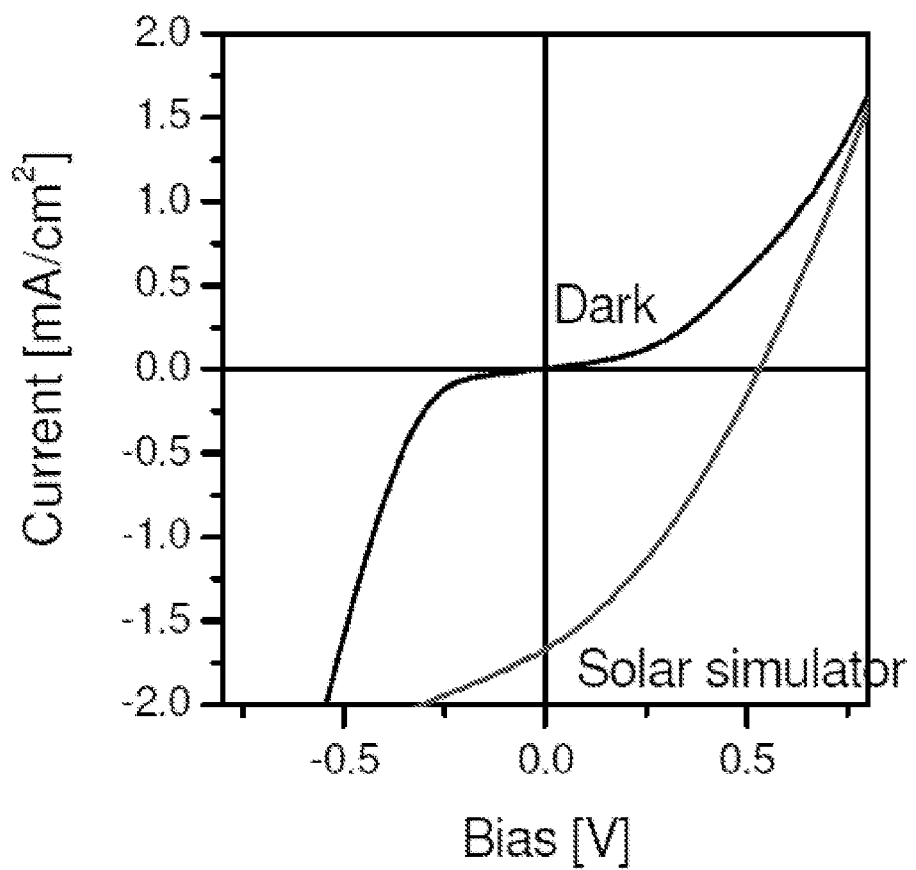
FIG. 14 shows the electrical current-voltage curve in the near-dark and with solar simulator illumination for a dye-sensitized solar cell that incorporates a solvent-washed mesoporous titania electrode according to an embodiment of the present invention.

The current between these electrodes was recorded as a function of the voltage between them. As illustrated in FIG. 14, the current measurements are shown under near-dark conditions and under illumination through the transparent substrate from a commercial solar simulator. The currents have been divided by the area of the cell. The measurements shown in FIG. 14 indicate a power generation in sunlight of about 0.4 $mW/cm^2$, corresponding to a solar conversion efficiency of about 0.4%.

While several embodiments of the invention have been discussed, it will be appreciated by those skilled in the art that various modifications and variations of the present invention are possible. Such modifications do not depart from the spirit and scope of the present invention.

What is claimed is:

1. A method for synthesizing a phosphonic acid functionalized mesoporous silica material comprising the steps of:
   (a) synthesizing a phosphonated triblock copolymer template;
   (b) self-assembling said phosphonated triblock copolymer with tetraethyl orthosilicate to form a mesoporous silica material attached to said phosphonated triblock copolymer template; and
   (c) extracting at least a portion of said mesoporous silica material from said phosphonated triblock copolymer template to form said phosphonic acid functionalized mesoporous silica material.

2. The method of claim 1, wherein said copolymer of said phosphonated triblock copolymer template is a poloxamer.

3. The method of claim 2, wherein said phosphonated poloxamer triblock copolymer template is acid cleavable.

4. The method of claim 1, wherein the step of synthesizing further comprises the step of converting terminal hydroxyl groups of poly(ethylene glycol) (PEG) blocks or of poly(ethylene oxide)-block-poly(propylene oxide)-block-poly(ethylene oxide) triblock copolymer to terminal phosphate ester groups.

5. The method of claim 4, wherein the step of converting further comprises the step of mixing said poly(ethylene oxide)-block-poly(propylene oxide)-block-poly(ethylene oxide) triblock copolymer with dimethylphosphite.

6. The method of claim 1, wherein the step of extracting further comprises the step of solvent washing.

7. The method of claim 6, wherein the step of solvent washing further comprises the step of undergoing hydrolysis at terminal phosphate ester groups of said mesoporous silica material attached to said phosphonated triblock copolymer template at a temperature of between about 50° C. and 80° C.

* * * * *